United States Patent [19]

Arai et al.

[11] Patent Number: 5,589,347
[45] Date of Patent: Dec. 31, 1996

[54] MULTILAYER ANALYSIS ELEMENTS FOR THE DETERMINATION OF TOTAL CHOLESTEROL

[75] Inventors: Fuminori Arai; Takeshi Igarashi, both of Saitama, Japan

[73] Assignee: Fuji Photo Film Co., Ltd., Kanagawa, Japan

[21] Appl. No.: 461,766

[22] Filed: Jun. 5, 1995

Related U.S. Application Data

[63] Continuation of Ser. No. 128,758, Sep. 30, 1993, abandoned, which is a continuation of Ser. No. 600,289, Oct. 19, 1990, abandoned, which is a continuation-in-part of Ser. No. 133,980, Dec. 17, 1987, abandoned.

[30] Foreign Application Priority Data

Dec. 18, 1986 [JP] Japan ................................. 61-302325

[51] Int. Cl.$^6$ ............................. C12Q 1/60; C12Q 1/44; C12N 11/00; G01N 33/92
[52] U.S. Cl. ................................. 435/11; 422/56; 435/18; 435/19; 435/25; 435/26; 435/28; 435/174; 435/175; 435/178; 435/180; 435/805; 436/71
[58] Field of Search ........................ 435/11, 18, 19, 435/23, 25, 26, 805, 810, 28, 174, 175, 178, 180; 436/71, 810, 824; 422/55, 56, 57, 60

[56] References Cited

U.S. PATENT DOCUMENTS

| | | | |
|---|---|---|---|
| Re. 29,498 | 12/1977 | Meiattini ................................. | 435/28 |
| 3,983,005 | 9/1976 | Goodhue et al. .......................... | 435/23 |
| 4,164,448 | 8/1979 | Roeschlaw et al. ...................... | 435/11 |
| 4,275,151 | 6/1981 | Esders et al. ............................. | 435/11 |
| 4,275,152 | 6/1981 | Esders et al. ............................. | 435/11 |
| 4,680,259 | 7/1987 | Cumbo et al. ............................ | 435/11 |
| 4,892,816 | 1/1990 | Akiba et al. .............................. | 435/11 |

FOREIGN PATENT DOCUMENTS

| | | |
|---|---|---|
| 0091026 | 10/1983 | European Pat. Off. . |
| 0176357 | 4/1986 | European Pat. Off. . |
| 0183381 | 4/1986 | European Pat. Off. ................. 435/11 |
| 0244825 | 11/1987 | European Pat. Off. . |

OTHER PUBLICATIONS

*Research Disclosure*, vol. 177, pp. 51–66 (Oct. 1974).
*Clinical Chemistry*, vol. 25, pp. 132–153 (Jan. 1979).
W. Tutz (ed). Textbook of Clinical Chemistry (W. B. Saunders Company Philadelphia) pp. 886–888 (1986).

*Primary Examiner*—David M. Naff
*Attorney, Agent, or Firm*—Sughrue, Mion, Zinn, Macpeak & Seas

[57] ABSTRACT

A multilayer analysis element for determination of total cholesterol is prepared having a light-transmissive water-impermeable support, at least one hydrophilic polymer layer on said support and a spreading layer on said hydrophilic polymer layer(s), and containing in one or more of the layers:

(a) at least one enzyme having cholesterol esterase activity, (b) cholesterol oxidase, (c) peroxidase, (d) a color reagent composition, which in the presence of hydrogen peroxide and the peroxidase, produces a color change (e) at least one bile acid compound selected from the group consisting of bile acids, bile acid derivatives and salts of said acids and derivatives, and (f) an alkyl phenoxy polyethoxy ethanol containing in the alkyl group 1 to 20, preferably 7 to 10 carbon atoms, and a polyoxyethylene chain composed of at least 16, preferably 30 to 60 oxyethylene units.

26 Claims, No Drawings

MULTILAYER ANALYSIS ELEMENTS FOR THE DETERMINATION OF TOTAL CHOLESTEROL

This application is a continuation of application Ser. No. 08/128,758, filed Sep. 30, 1993, now abandoned, which is a continuation of application Ser. No. 07/600,289, filed Oct. 19, 1990, now abandoned, which is a continuation-in-part of application Ser. No. 07/133,980, filed Dec. 17, 1987, now abandoned.

FIELD OF THE INVENTION

This invention relates to an improvement in a dry type multilayer analysis element for quantitatively analyzing total cholesterol contained in aqueous samples, such as body fluids (e.g., blood), food and drinks.

BACKGROUND OF THE INVENTION

In the quantitative analysis of cholesterol and cholesterol esters which are present in the form of lipoproteins in body fluids such as blood, by using a dry type multilayer analysis element, blood, as an aqueous sample, is used without being diluted with water, physiological saline, a pH buffer, etc. Hence, the color reaction in the analysis element does not proceed rapidly. Further, substances in the body fluid (e.g., neutral fats in the blood), make accurate analysis difficult.

In the attempt to solve the above problem, Japanese Patent Application (OPI) Nos. 96378/78 and 85200/86 (corresponding English literatures are shown hereinafter) and CLINICAL CHEMISTRY, 28, 1159–1162 (1982) proposed the joint use of an alkyl phenoxy polyethoxy ethanol. (The term "OPI" indicates an unexamined published patent open to public inspection.) However, techniques proposed in these references have been found to have the following problems:

(1) Cholesterol esterase activity is inhibited.
(2) During storage before use, the dry type multilayer analysis element has a strong tendency to absorb water. Hence, the enzyme activity in the element is decreased or lost, and the performance of the element is degraded.

CLINICAL CHEMISTRY, 20, 470–475 (1974) and Japanese Patent Application (OPI) No. 125796/75 describe that cholesterol esters are efficiently hydrolyzed in aqueous solution by using cholesterol esterase and bile acid or its salt in combination. When this technique is applied to the dry type multilayer analysis element, spreading of an aqueous sample, particularly blood (whole blood, plasma or serum) is poor on a porous spreading layer, and the accuracy of analysis decreases drastically.

SUMMARY OF THE INVENTION

Accordingly an object of the present invention is to provide an excellent dry type multilayer analysis element for total cholesterol determination which offers a solution to the aforesaid problems (such as the inhibition of cholesterol esterase activity, the degraded performance during storage, and the low accuracy of analysis).

In order to solve the above-described problems, it has been found that by using a cholesterol analysis reagent composition comprising a combination of bile acid or its salt with an alkyl phenoxy polyethoxy ethanol containing a polyoxyethylene chain with at least 16 (and usually at least 20 on an average) oxyethylene units, a dry type multilayer analysis element can be obtained where inhibitions of the activity of an enzyme having cholesterol esterase activity is decreased and which has increased storage stability.

It has also been found that when a liquid sample containing various substances which interfere with the coloration of the colorimetric reagent composition, such as blood (whole blood, plasma, or serum), is used, the color reaction proceeds smoothly if carried out in the presence of bile acid or its salt and an alkyl phenoxy polyethoxy ethanol containing a polyoxyethylene chain with at least 16 (and generally at least 20 on an average) oxyethylene units, and that as a result, a high optical density of the coloration can be obtained which permits accurate colorimetry of the total cholesterol content of the sample.

According to this invention, there is provided an improved dry type multilayer analysis element for determination of total cholesterol comprising a light-transmissive water-impermeable support, at least one hydrophilic polymer layer (to be referred to as a hydrophilic layer) on said support and a spreading layer on said hydrophilic polymer layer(s) and further containing a cholesterol analysis reagent composition comprising at least one enzyme having cholesterol esterase activity, cholesterol oxidase, peroxidase and a colorimetric reagent composition in at least one of said spreading layer and the hydrophilic polymer layer(s), wherein said element further includes a bile acid compound (at least one of bile acids, bile acid derivatives and salts thereof) and an alkyl phenoxy polyethoxy ethanol containing polyoxyethylene chains with at least 16 (and generally at least 20 on an average) oxyethylene units are included in at least one of the spreading layer and the hydrophilic layer(s).

DETAILED DESCRIPTION OF THE INVENTION

The element of the present invention usually forms an integral multilayer analysis element.

The light-transmissive water-impermeable support used in this invention may be any of those used generally in multilayer analysis elements. Specifically, there may be used, for example, a transparent support having a thickness of about 50 pm to about 1 mm, preferably about 80 μm to about 300 μm, made of a polymer such as polyethylene terephthalate, bisphenol A, polycarbonate, polystyrene, and cellulose esters (e.g., cellulose diacetate, cellulose triacetate and cellulose acetate propionate). As required, the adhesion of the support to the hydrophilic layer and other layers to be provided on the support can be strengthened by providing a subbing layer or an adhesive layer known from the specifications of the above-cited patent documents.

A hydrophilic layer can be allowed to function as a water-absorbing layer which does not contain a reagent component, swells upon water absorption, and optionally may receive a species to be detected (a dye formed) and accumulate it, and as a detecting layer which contains a mordant having a negative or a positive charge and being able to receive and fix the species to be detected and swells upon water absorption. This layer may contain a pH buffer composition which stabilizes the pH at the time of the color reaction. It may be formed of a hydrophilic polymer binder alone or with another component containing therein. The hydrophilic polymer binder is a natural or synthetic hydrophilic polymer having a swelling ratio at the time of water absorption of about 150% to about 2000%, preferably about 250% to about 1500%, at 30° C.

Examples of the hydrophilic polymer binder include gelatins (acid-processed gelatin, deionized gelatin, etc.), gelatin derivatives (such as phthalated gelatin, and hydroxyacrylate grafted gelatin), agarose, pullulan, pullulan derivatives, polyacrylamide, polyvinyl alcohol, and polyvinylpyrrolidone, as disclosed, for example, in Japanese Patent Application (OPI) Nos. 171864/84 and 108753/85.

The hydrophilic layer generally has a thickness in the dry state of about 1 μm to about 100 μm, preferably about 3 μm to about 50 μm, especially preferably about 5 μm to about 30 μm, and is preferably substantially transparent.

The hydrophilic layer may include some or all of a pH buffer, enzymes, a colorimetric reagent composition and an optional reagent (such as a ferrocyanide which is used to increase a coloring speed and increase a coloring efficiency), and also one or more of known mordants, basic polymers (acts as a basic buffer or a base), acidic polymers (acts as an acidic polymer or an acid), etc. In this case, the hydrophilic layer functions as a reagent layer or a coloring reagent layer.

Examples of the spreading layers include non-fibrous isotropic porous developing layers such as a porous layer containing continuous open microvoids in which a membrane filter (a blushed polymer layer), and polymeric microbeads, glass microbeads and diatomaceous earth held in a hydrophilic polymer binder disclosed, for example, in Japanese Patent Publication No. 21677/78, and a porous layer containing continuous open microvoids (a three-dimensional lattice particle structure layer) in which polymeric microbeads and glass microbeads are bonded in point-to-point contact with a polymer adhesive not swellable with water as disclosed in Japanese Patent Application (OPI) No. 90859/80; fibrous porous layers such as the spreading layers of woven fabrics disclosed, for example, in Japanese Patent Application (OPI) Nos. 164356/80 and 66359/82; the spreading layer of knitted fabric disclosed in Japanese Patent Application (OPI) No. 222769/85, and spreading layer composed of paper containing organic polymer fiber pulp disclosed in Japanese Patent Application (OPI) No. 148250/82.

The spreading layer is superimposed on the hydrophilic layer either directly or as required, through an adhesive layer. The spreading layer may include a part or all of the enzymes, the colorimetric reagent composition and as required, a ferrocyanide and other reagents.

Of the enzymes, one having cholesterol esterase activity is preferably included in the porous spreading layer.

In the multilayer analysis element of this invention, there may be incorporated reagent layers, light-shielding layers, light-reflecting layers, filtration layers, semipermeable layers, barrier layers and diffusion preventing layers (migration preventing layers) as disclosed in the above-cited patent documents, and a layer having two or more functions possessed by single layer of these layers.

The reagent layers contains a part or all of the enzymes, the colorimetric reagent composition and as required, the ferrocyanide and other reagents. It is a non-porous water absorbing and preferably swellable or a microporous water-permeable layer. It is a preferable embodiment that a water-absorbing layer is provided on a support and a reagent layer is provided thereon.

A hydrophilic polymer binder used in the substantially non-porous water-absorbing reagent layer acts as a medium for dissolving or dispersing the reagent substantially uniformly and at least has an action of absorbing water from the liquid analysis sample and transporting the component to be analyzed to the reagent layer together with water. The hydrophilic polymer binder may be any one of the water-absorbing hydrophilic polymer binders used in the aforesaid hydrophilic layer. The substantially non-porous reagent layer has a thickness in the dry state generally of about 3 μm to about 50 μm, preferably about 5 μm to about 30 μm, and the reagent layer is preferably substantially transparent.

The microporous water-permeable reagent layer is a layer in which a reagent or a reagent compositions is included in a microporous structure layer consisting of solid fine particles and a hydrophilic polymer binder therefor. The microporous structure layer, as referred to herein, is a layer of a structure composed of microporous fine particles of non-porous fine particles and a hydrophilic polymer binder bonding the fine particles to one another to retain a microporous open void structure.

Examples of the microporous fine particles or the non porous fine particles used in the porous reagent layer are cellulose particles such as fine powders or fine particles of cellulose or microcrystalline cellulose, fine particles of silicon dioxide compounds, such as silica, and diatomaceous earth, fine particles of silicates, such as zeolite, polymer microbeads, glass microbeads, and various ceramic beads. The hydrophilic polymer binder may be properly selected from the same polymers as the water-absorbing hydrophilic polymers used in the above-described hydrophilic layer, and the aqueous lattices of copolymers containing about 2% or more of hydrophilic recurring units as disclosed in Japanese Patent Application (OPI) No. 145965/84 may also be used. The microporous reagent layer has a thickness in the dry state generally of about 7 μm to about 50 μm, preferably about 10 μm to about 30 μm.

The reagent layer may include known pH buffer compositions, polymeric pH buffers, basic polymers, acid polymers, polymeric mordants, etc.

In one preferred embodiment, a water-absorbing layer is disposed between the reagent layer and the support. In an especially preferred embodiment, the colorimetric reagent composition is included in the hydrophilic layer, and the enzyme, the bile acid compound and the alkyl phenoxy polyethoxy ethanol are included in the porous spreading layer.

A light-shielding layer may be provided on the reagent layer or any other hydrophilic layer. The light-shielding layer is a water-permeable or water-penetrable layer composed of fine particles or powders (to be simply referred to as fine particles) having a light-shielding property or both light-reflecting and light-reflecting properties dispersed and retained in a small amount of a film-forming hydrophilic polymer binder. The light-shielding layer shields the color of the aqueous liquid sample, particularly, the red color of hemoglobin contained in a whole blood sample, spotted and fed onto the spreading layer when the color formed in the reagent layer or the hydrophilic layer is reflected and measured from the side of the light-transmissive support. It also acts as a light reflecting layer or a background layer.

Examples of the fine particles having both light-shielding and light-reflecting properties are fine particles of titanium dioxide (fine crystalline particles having a particle diameter of from about 0.1 μm to about 1.2 μm of rutile, anatase or brookite type titanium dioxide), fine particles of barium sulfate, and fine particles or fine flakes of aluminum. Among these, fine particles of titanium dioxide and fine particles of barium sulfate are preferred.

Examples of the light-shielding fine particles are carbon black, gas black and carbon microbeads.

The film-forming hydrophilic polymer binder may be the same hydrophilic polymers as used in the hydrophilic layer, and also weakly hydrophilic regenerated cellulose and cellulose acetate. Preferred polymer binders are gelatin, gelatin derivatives and polyacrylamide. The gelatin and gelatin derivatives may be used as a mixture with known hardeners (crosslinking agents).

The light-shielding layer may by provided by coating an aqueous dispersion of light-shielding fine particles and a hydrophilic polymer on the reagent layer or the hydrophilic layer and drying it by a known method. The volume ratio of the hydrophilic polymer binder to 10 parts of the light-shielding fine particles in the dry state is generally from about 2.5 to about 7.5 preferably from about 3.0 to 6.5 parts. When the light-shielding fine particles are those of titanium dioxide, the weight ratio of the polymer binder to 10 parts of fine particles of titanium dioxide is from about 0.6 to about 1.8, preferably about 0.8 to 1.5 parts. The thickness of the light-shielding layer on drying is generally from about 3 μm to about 30 μm, preferably from about 5 μm to about 20 μm.

An adhesive layer may be provided to stack and bond the spreading layer, the light-shielding layer, etc. When a porous spreading layer is provided on the light-shielding layer, it is preferable to provide the adhesive layer. However, when a spreading layer is provided on a hydrophilic polymer-containing layer such as water-absorbing layer, a reagent layer, etc., the adhesive layer may not be provided depending on the type and properties of the hydrophilic polymer. The adhesive layer is composed mainly of a hydrophilic polymer which when wetted with water or swollen with water, can bond the spreading layer to form a integral structure. The hydrophilic polymer used in the adhesive layer may be any of the same hydrophilic polymers used in the above-described hydrophilic layer. Preferred hydrophilic polymers used in the adhesive layer are gelatin, gelatin derivatives, polyvinyl alcohol and polyacrylamide. The adhesive layer has a thickness in the dry state generally of about 0.5 μm to about 20 μm, preferably about 1 μm to about 10 μm. The adhesive layer may contain a surface-active agent, preferably a nonionic surface-active agent such as a nonionic surface-active agent having a chain structure composed of 8 to 15 oxyethylene or oxypropylene groups linked to each other.

The adhesive layer may be provided by coating an aqueous solution containing a hydrophilic polymer and as optional components, the surface-active agent, etc., on the reagent layer, the hydrophilic layer or on the light-shielding layer by a known method.

The cholesterol analysis colorimetric reagent composition used in the element of this invention comprises at least one enzyme having cholesterol esterase activity, cholesterol oxidase, peroxidase, a colorimetric reagent composition, at least one compound selected from the group consisting of bile acids, bile acid derivatives and salts thereof, and an alkyl phenoxy polyethoxy ethanol containing a polyoxyethylene chain composed of at least 16 (and generally at least 20 on an average) oxyethylene units. The composition may also contain a ferrocyanide.

The cholesterol esterase (Enzyme Code 3.1.1.13; hereinafter "Enzyme Code" is simply referred to as "EC") is an enzyme which converts cholesterol esters in the analysis sample into cholesterol. Cholesterol oxidase (EC 1.1.3.6) is an enzyme which oxidizes cholesterol to form hydrogen peroxide. Peroxidase (EC 1.11.1.7) is an enzyme which participates in an reaction of oxidizing the colorimetric reagent composition by utilizing hydrogen peroxide to form a color. Not only enzymes classified as EC 3.1.1.13 may be used as the cholesterol esterase, but there can also be used other enzymes having cholesterol esterase activity either singly (for example, lipase, such as LIPASE M (trade name) manufactured by Enzyme Development Corp. and LIPASE 3000 (trade name) manufactured by Wilson Laboratories as described in Japanese Patent Publication No. 45599/1981) or combinations of two or more such enzymes, for example, a combination of lipase having cholesterol esterase activity described in Japanese Patent Publication No. 45599/81 (e.g., LIPASE M and LIPASE 3000) with protease, for example, chymotrypsin (EC 3.4.21.1), papain (EC 3.4.21.2), or bromelain (EC 3.4.22.4), or PRONASE trademark; a kind of protease manufactured by Sigma Chemical Co.).

Cholesterol oxidase (EC 1.1.3.6) is an enzyme which oxidizes cholesterol to generate hydrogen peroxide. It may be selected properly from commercially available enzymes. As required, it may be used together with a coenzyme such as FAD (flavin adenine dinucleotide).

As the peroxidase, peroxidases (EC 1.11.1.7) derived from a plant or an animals described in Japanese Patent Publications No. 45599/1981 and 5520/1982, and a peroxidase (EC 1.11.1.7) or derived from a microorganism as described in Japanese Patent Publications No. 5035/1983 may be used. Of these, non-specific peroxidases derived from plant or microorganism are preferred. Examples of the preferred peroxidases are peroxidases extracted from horseradish and radish, and peroxidases extracted from microorganisms of the genera Cochliobolus and Curvularia.

Examples of the bile acids are cholic acid, deoxycholic acid, lithocholic acid, and kenodeoxycholic acid. Examples of the bile acid derivatives are taurocholic acid, glycocholic acid, taurodeoxycholic acid, and glycodeoxycholic acid. The salts of the bile acids and bile acid derivatives may, for example, be sodium, potassium and lithium salts of these compounds. In the multilayer analysis element of this invention, at least one compound selected from the above-mentioned bile acids, and bile acid derivatives and their salts (to be generally referred to as the bile acid compounds in this invention) is included in any of the layers. Preferably, the bile acid compound is included in the layer or in a layer adjoining the spreading layer. Especially preferably, the bile acid compound is included in the same layer together with the alkyl phenoxy polyethoxy ethanol and one or more of enzymes having cholesterol esterase activity.

The alkyl groups in the alkyl phenoxy polyethoxy ethanol containing a polyoxyethylene chain composed of at least 16 (and generally at least 20 on an average) oxyethylene units (to be referred to simply as the alkyl phenoxy polyethoxy ethanol; this compound is also called a polyoxyethylene alkylphenyl ether) may be various alkyl groups, preferably linear or branched alkyl groups having from 1 to 20, more preferably from 7 to 10 carbon atoms, and the most preferably having 8 or 9 carbon atoms such as an octyl, 1,1,3,3-tetramethylbutyl or nonyl group. The number of the oxyethylene units in the polyoxyethylene chain is from preferably 16 to about 60, and the average number of the units is preferably from 20 to 50 and more preferably from 30 to 50. The alkyl group may be present at any position of the phenyl group, however, generally, it is at p- or m-position with respect to the oxygen atom of the phenoxy group.

Examples of the alkyl phenoxy polyethoxy ethanol are octyl phenoxy polyethoxy ethanol (a mixture of compounds containing 20 to 40 oxyethylene units on an average), nonyl phenoxy polyethoxy ethanol (containing 20 to 40 oxyethylene units on an average), 1,1,3,3-tetramethyl butyl phenoxy polyethoxy ethanol (containing 20 to 40 oxyethylene units on an average). Preferably, the alkyl phenoxy polyethoxy ethanol is included in the same layer together with one or more enzymes having cholesterol esterase activity and the bile acid compound or in a layer adjacent to the layer containing enzymes and the bile acid compound. Two or more alkyl phenoxy polyethoxy ethanols may be used in combination, or one or more of alkyl pyhenoxy polyethoxy ethanols may be used in combination with another type of surface-active agent, particularly a nonionic surface-active agent.

The colorimetric reagent composition is, for example, (1) a composition containing a chromogen and a coupler, and oxidatively couples with the chromogen by hydrogen peroxide in the presence of peroxidase to coloring by forming a quinoneimine dye, or (2) a leuco dye which is oxidized by hydrogen peroxide in the presence of peroxidase to form a dye.

Examples of the chromogen are 4-aminoantipyrine (also called 4-aminophenazone, i.e., 1-phenyl-2,3-dimethyl-4-amino-3-pyrazoline-5-one) described in Ann. Clin. Biochem, 6, 24–27 (1969), trisubstituted-4-amino-3-pyrazoline-5-ones such as 1-(2,4,6-trichlorophenyl)-2,3-dimethyl-4-amino-3-pyrazoline-5-one) and 1-(3,5-dichlorophenyl)-2,3-dimethyl-4-amino-3-pyrazoline-5-one described in Japanese Patent Application (OPI) No. 54962/1984, and 4-aminoantipyrine analogs such as 1-phenyl-2,3-dimethyl-4-dimethylamino-3-pyrazoline-5-one described in Japanese Patent Publication No. 25840/1980. Of these, 4-aminoantipyrine, 1-(2,4,6-trichlorophenyl)-2,3-dimethyl-4-amino-3-pyrazoline-5-one and 1-(3,5-dichlorophenyl)-2,3-dimethyl-4-amino-3-pyrazoline-5-one) are preferred.

Examples of the couplers include the phenols described in Ann. Clin. Biochem., 6, 24–27 (1969), Japanese Patent Publications Nos. 25840/1980, 45599/1981 and 18628/1983, Japanese Patent Application (OPI) Nos. 164356/1980, 124398/1981 and 155852/1981; phenolsulfonic acids (including alkali metal salts and alkaline earth metal salts thereof) such as 2-hydroxy-1-benzenesulfonic acid, 4-hydroxy-1-benzenesulfonic acid, 3,5-dichloro-2-hydroxy-1-benzenesulfonic acid and 2-hydroxy-3-methoxy-1-benzenesulfonic acid; 1-naphthol and 2-naphthol; dihydroxynaphthalenes such as 1,7-dihydroxynaphthalene; naphtholsulfonic acids (including alkali metal salts and alkaline earth metal salts thereof) such as 1-hydroxy-2-naphthalenesulfonic acid and 1-hydroxy-4-naphthalenesulfonic acid; and other phenol or naphthol derivatives. Of these compounds, 1, 7-dihydroxynaphthalene, 1-hydroxy-2-naphthalenesulfonic acid (including its Na, K and Li salts) and 3,5-dichloro-2-hydroxy-1-benzenesulfonic acid (including its Na, K and Li salts).

Examples of the leuco dye are triarylimidazole leuco dyes such as 2-(4-hydroxy-3,5-dimethoxyphenyl)-4,5-bis[4-(dimethylamino)phenyl]imidazole described in Japanese Patent Publication No. 5519/1982; diarylimidazole leuco dyes such as 2-(3,5-dimethoxy-4-hydroxyphenyl)-4-[4-(dimethylamino)phenyl]5-phenethylimidazole described in Japanese Patent Application (OPI) No. 193352/1984; diarylindolylimidazole leuco dyes such as 2-(2-phenyl-3-indolyl)-4,5-di[4-(dimethylamino)phenyl]-imidazole described in Japanese patent Application (OPI) No. 960/1986; triarylmonoacylimidazole leuco dyes such as 2-(4-hydroxy-3,5-dimethoxyphenyl)-3-acetyl-4,5-bis[4-(diethylamino)phenyl]imidazole described in Japanese Patent Application (OPI) No. 229868/1986; and triarylmonoalkylimidazole leuco dyes such as 2-(4-hydroxy-5-dimethoxyphenyl)-3-methyl-4,5-bis[4-(diethylamino)phenyl]imidazole.

A ferrocyanide compound may be added as an optional component to the cholesterol analysis colorimetric reagent composition.

A compound which contains or releases a ferrocyanide ion (a hexacyanoferrate (II) ion, i.e., $[FE(CN)_6]^{4\ominus}$ may be used as the ferrocyanide compound. Alkali metal or alkaline earth metal hexacyanoferrates (II) or mixture of these metal salts may be used as the ferrocyanide compound. Specific examples of the ferrocyanide compound are sodium ferrocyanide $Na_4[Fe(CN)_6]$, potassium ferrocyanide $K_4[Fe(CN)_6]$, lithium hexacyanoferrate (II), magnesium hexacyanoferrate (II), and calcium hexacyanoferrate (II). Of these, potassium ferrocyanide and sodium ferrocyanide are preferred.

Among the components of the cholesterol analysis colorimetric reagent composition, the enzymes, the bile acid compound and the alkyl phenoxy polyethoxy ethanol are preferably included in the porous spreading layer. The colorimetric reagent composition and the ferrocyanide as an optional component may be included in one or more of the porous spreading layer and a layer adjoining or not adjoining the porous spreading layer such as an independent reagent layer, a hydrophilic layer and a water-absorbing layer.

The amounts of the components of the cholesterol analysis colorimetric reagent composition used in the element of the present invention (the amounts coated per $m^2$ of the element) are as follows:

At least one enzyme having cholesterol esterase activity: about 500 to about 50,000 IU, preferably about 1,000 to about 30,000 IU (as the cholesterol esterase activity value).

Cholesterol oxidase: about 1,000 to about 30,000 IU, preferably about 1,500 to about 20,000 IU.

Peroxidase: about 1,000 to about 100,000, preferably about 2,000 to about 60,000 IU.

Chromogen or leuco dye: about 0.5 to about 10 millimoles, preferably about 1 to 5 millimoles.

Coupler: about 2.5 to about 50 millimoles, preferably about 5 to about 25 millimoles.

Ferrocyanide: about 0.1 to about 10 millimoles, preferably about 0.5 to about 5 millimoles.

Bile acid compound: about 0.2 g to about 10.0 g, preferably about 0.5 to about 5.0 g.

Alkyl phenoxy polyethoxy ethanol containing a polyoxyethylene chain composed of at least 16 (and generally at least 20 on an average) oxyethylene units: about 0.5 g to about 12.0 g, preferably about 0.8 g to about 8.0 g.

A known buffer capable of buffering the pH values at the time of conducting analysis of a liquid sample to a desired value in the range of about 5.5 to about 9.0, preferably about 7.7 to about 8.5, may be included in the multilayer analysis element of the present invention.

Buffers that can be used are, for example, the pH buffer systems described in "Manual of Chemistry, Fundamentals" edited by the Japanese Chemical Society (published in 1966 by Maruzen Co., Ltd., Tokyo), pages 1312–1320; "Data for Biochemical Research" edited by R. M. C. Dawson et al., 2nd edition (published by Oxford at the Clarendon Press, 1969), pages 476–508, Biochemistry 5, page 467 et seq., (1966) and Analytical Biochemistry, 104, pages 300–310 (1980).

Specific examples of pH buffers within a pH range of 5.5 to 9.0 include buffers containing tris(hydroxymethyl)aminomethane (Tris); buffers containing phosphates; buffers containing borates; buffers containing citric acid or citrates; buffers containing glysine; N,N-bis(2-hydroxyethyl)glycine (Bicine); a Na or K salt of N-2-hydroxyethylpiperazine-N'-2-hydroxypropane-3-sulfonic acid (HEPPS); a Na or K salt of N-2-hydroxyethylpiperazine-N'-3-sulfonic acid (EPPS); a Na or K salt of N-[tris(hydroxymethyl)methyl]-3-aminopropanesulfonic acid (TAPS); a Na or K salt of N-2-hydroxyethylpiperazine-N'-2-ethanesulfonic acid (HEPES); and acids, alkalis or salts to be combined with any of these above compounds as required. Specific examples of preferred buffers are potassium dihydrogen phosphate-disodium hydrogen phosphate; Tris-sodium borate; Tris-sodium borate-EDTA-2Na salt; Tris-citric acid; citric acid-sodium dihydrogen phosphate; Bicine; HEPPS; HEPPS sodium salt: EPPS; EPPS sodium salt; TAPS; TAPS sodium salt.

Preferably, the pH buffer is included in the layer containing an enzyme. The pH buffer is preferably included in the porous spreading layer or the reagent layer containing the enzyme. On the other hand, a low-molecular-weight pH buffer can move through layers with the penetration of water which is a medium for the applied aqueous liquid sample, and therefore does not have to be contained in all of the layers containing the enzyme and the colorimetric reagent composition. Such a low-molecular-weight pH buffer may be included only in the hydrophilic layer or the water-absorbing layer, for example.

Preferably, from the standpoint of production, packing, transportation, storage and analyzing operation, the multilayer analysis element of this invention is cut into small pieces in the shape of a square having one side measuring from about 15 mm to about 30 mm or in the shape of a circle having much the same size, and formed into analyzing slides by setting them into slide frames as disclosed, for example, in Japanese Patent Application (OPI) Nos. 63452/1982, and 156079/1979, Japanese Utility Model Application (OPI) Nos. 142454/1981 and 32350/1983 and Japanese Patent Application Publication No. 501144/1983 (based on PCT Application).

The analysis sample may be any aqueous sample containing cholesterol, and may include, for example, blood samples such as whole blood, plasma or serum samples, other various body fluids, foods, and process controlling samples for plants which produce or utilize cholesterol.

In accordance with the methods described in the above-cited patent documents, about 5 µl to about 30 µl, preferably about 8 µl to about 15 µl, of the aqueous liquid sample is spotted on the spreading layer of the multilayer analysis element, and as required incubated at a substantially constant temperature in the range of about 20° C. to about 45° C., preferably about 35 ° C., to about 40 ° C. Thereafter, the color formed in the analysis element is reflected and measured, for example, from the side of the light-transmissive support, and on the principle of reflectometry, the total cholesterol content of the liquid sample can be determined.

The following examples are given for illustrative purposes only and are in no way intended to limit the scope of the present invention.

EXAMPLE 1

On a polyethylene terephthalate (PET) film, 180 micrometers thick having a gelatin subbing layer, gelatin (26 g/m²), nonyl phenoxy polyethoxy ethanol (containing an average number of oxyethylene units within the range of from 9 to 10; the number of oxyethylene units will be abbreviated hereinbelow as n) (0.03 g/m²) and bis(vinylsulfonylmethyl) ether (30 mg/m²) were coated and dried to form a gelatin layer (water-absorbing layer).

Water was supplied as moistening water to the water-abosrbing layer at a rate of 30 g/m², and a tricot knitted fabric (average thickness 250 µm) composed of spun yarns (50 denier) of polyethylene terephthalate (PET) rendered hydrophilic by glow discharge was laminated and bonded to form a spreading layer.

Then, an aqueous solution of a cholesterol analysis colorimetric reagent composition was coated on the knitted fabric spreading layer and dried so that the coating amounts of its components in the spreading layer were as shown below. Thus, a multilayer analysis element for total cholesterol determination was produced.

| The amounts of the components of the cholesterol analysis colorimetric reagent composition (per m²) | |
|---|---|
| Methyl cellulose (methoxy group content 29%, viscosity 112 cps as a 2% by weight aqueous solution at 20° C.) | 3.0 g |
| Fine particles of titanium dioxide (rutile type; particle size 0.25–0.40 µm) | 24 g |
| Octyl phenoxy polyethoxy ethanol (n = 40 on an average) | 1.1 g |
| Sodium deoxycholate | 1.5 g |
| Cholesterol oxidase (EC 1.1.3.6) | 3500 IU |
| Cholesterol esterase (EC 3.1.1.13) | 2000 IU |
| Peroxidase (EC 1.11.1.7) | 2900 IU |
| Sodium 2-hydroxy-3,5-bichloro-benzenesulfonate | 1.8 g |
| 4-Aminoantipyrine | 0.3 g |
| Sodium dihydrogen phosphate | 7.3 g |
| NaOH to adjust the pH to 8.0 | |

Comparative Example 1

Example 1 was repeated except that octyl phenoxy polyethoxy ethanol (n=40 on an average), nonyl phenoxy polyethoxy ethanol (n=within the range of 9–10 on an average) and sodium deoxycholate were changed in amounts or newly added as indicated in Table 1 below in 9 different cases. Thus, comparative multilayer analysis elements for total cholesterol determination were produced.

Each of the multilayer analysis elements produced in Example 1 and Comparative Example 1 was cut into a square chip having a size of 15 mm×15 mm, and set in a plastic mount of the type disclosed in Japanese Patent Application (OPI) NO. 63452/1982 to form a chemical analysis slide for the determination of total cholesterol.

These slides were evaluated in the following manner.

Experiment-1

The above-described chemical analysis slide was stored for 3 days at 4° C. at a relative humidity of not more than 5%, and at 45° C. and a relative humidity (RH) of about 45%. Optical Reflectance densities of the colors formed were compared. 10 µl of a human plasma sample having a cholesterol concentration of about 450 mg/dl taken by using heparin was spotted on each slide and incubated at 37° C. for 6 minutes. The reflecting optical density was measured from the side of the PET support with light having a wavelength of 540 nm.

Experiment-2

The total cholesterol levels of human plasma samples having different total cholesterol levels were measured by the solution method of C. C. Allain et al. as a standard method [CLINICAL CHEMISTRY, 20, 470–475, (1974)]. On the basis of the results obtained, a calibration curve for human plasma was prepared for the multilayer analysis elements of the present invention and the comparisons.

Using human plasma having a neutral fat concentration of about 620 mg/dl, the same operation as in Experiment-1 was performed to form the colored product. The total cholesterol content was determined from the calibration curve.

Experiment-3

Using human plasma having a total protein content of about 11 g/dl, the same operation as in Experiment-1 was performed, and the colored product was formed. The total cholesterol content was determined from the above calibration curve.

The Table below summarizes the ratios of the total cholesterol content obtained by the chemical analysis slide to that obtained by the method of Allain et al. in human plasma samples in Experiment-2 and Experiment-3.

The results given in Table 1 below clearly show that (1) the multilayer analysis elements for total cholesterol determination in accordance with this invention have very small decrease (less than 1.3%) in the optical reflectance densities of the colored product even after the accelerated deterioration test at 45° C. and 45% RH for 3 days; (2) as in the solution method of C. C. Allain et al. as the standard measuring method, interference of the analysis due to neutral fats in the blood (about −1%) and total proteins in the blood (about −3%) is negligible with the elements of the present invention; and as overall properties, the element of the present invention have a very good correlation with the standard method.

In Table 2 it can be seen that when component (e) or component (f) is not included in the colorimetric reagent composition, poor results are obtained. On the other hand, when both of components (e) and (f) are used, synergistic effects are obtained. This can be seen especially clearly by comparing the results obtained in Example 2-5 and those in Comparative Examples 2-1 and 2-3.

Patent documents written in English and corresponding to Japanese Patent documents referred hereinabove are listed below.

JPA=Japanese Patent Application (OPI)
JPP=Japanese Patent Publication
UMP=Utility Model Application (OPI)

TABLE 1

| Multilayer analysis element | Example 1 Invention | Comparative Example | | | | | | | | |
|---|---|---|---|---|---|---|---|---|---|---|
| | | 1-1 | 1-2 | 1-3 | 1-4 | 1-5 | 1-6 | 1-7 | 1-8 | 1-9 |
| NPhPEE n: average 9–10 | 0.03 g | 7.0 g | 15 g | 0.03 g | 0.03 g | 0.03 g | 0.03 g | 0.03 g | 7.0 g | 15 g |
| OPhPEE n: average 40 | 1.1 g | — | — | — | 1.5 g | 6.0 g | — | — | — | — |
| Sodium deoxycholate | 1.5 g | — | — | — | — | — | 1.5 g | 6.0 g | 4.0 g | 4.0 g |
| Experiment-1 | | | | | (Reflection optical density values) | | | | | |
| 4° C., not more than 5% RH | 0.852 | 0.791 | 0.760 | 0.610 | 0.720 | 0.740 | 0.772 | 0.792 | 0.780 | 0.760 |
| 45° C. 45% RH | 0.841 | 0.701 | 0.521 | 0.603 | 0.710 | 0.709 | 0.770 | 0.784 | 0.623 | 0.592 |
| Difference between 4° C. and 45° C. | 0.011 | 0.090 | 0.239 | 0.007 | 0.010 | 0.031 | 0.002 | 0.008 | 0.157 | 0.168 |
| Experiment-2 | | | | | | | | | | |
| Ratio to the Allain method | 0.99 | 1.0 | 0.98 | 0.62 | 0.84 | 0.82 | 0.97 | 0.95 | 0.96 | 0.98 |
| Experiment-3 | | | | | | | | | | |
| Ratio to the Allain method | 0.97 | 0.92 | 0.93 | 0.71 | 0.94 | 0.96 | 0.82 | 0.87 | 0.91 | 0.94 |

Note:
OPhPEE: octyl phenoxy polyethoxy ethanol
NPhPEE: nonyl phenoxy polyethoxy ethanol Example 2 and Comparative Example 2

The same experiment was conducted as Example 1 except that 0.03 g/m² of nonyl phenyl polyglycidyl ether was used instead of nonyl phenoxy polyethoxy ethanol, and the amounts of the components were changed as shown in Table 2. The results are shown in Table 2.

TABLE 2

| Multilayer Analysis Element | Example 2 | | | | | | Comparative Example | | | |
|---|---|---|---|---|---|---|---|---|---|---|
| | 2-1 | 2-2 | 2-3 | 2-4 | 2-5 | 2-6 | 2-1 | 2-2 | 2-3 | 2-4 |
| Peroxidase (IU) | 2,900 | 2,900 | 70,000 | 2,900 | 70,000 | 70,000 | 70,000 | 70,000 | 70,000 | 70,000 |
| NPhPEE (g) (n: average 9–10) | — | — | — | — | — | — | — | — | — | — |
| OPhPEE (g) (n: average 40) | 1.1 | 1.1* | 1.1 | 1.1 | 4 | 6 | 7 | 15 | — | — |
| Sodium deoxycholate (g) | 1.5 | 1.5 | 1.5 | 1.5 | 3 | 2 | 0 | 0 | 7 | 15 |
| K$_4$[Fe(CN)$_6$] (g) | 0.2 | — | — | — | — | — | — | — | — | — |
| Experiment-1 | | | | | | | | | | |
| 4° C., not more than 5% RH | 0.895 | 0.862 | 0.850 | 0.851 | 0.873 | 0.886 | 0.743 | 0.738 | 0.790 | 0.799 |
| 45° C., 45% RH | 0.883 | 0.850 | 0.842 | 0.843 | 0.862 | 0.877 | 0.711 | 0.715 | 0.786 | 0.784 |
| Difference between 4° C. and 45° C. | 0.012 | 0.012 | 0.008 | 0.008 | 0.011 | 0.009 | 0.032 | 0.023 | 0.004 | 0.015 |
| Experiment-2 | | | | | | | | | | |
| Ratio to the Allain method | 0.99 | 0.98 | 0.98 | 0.99 | 0.98 | 0.99 | 0.85 | 0.82 | 0.93 | 0.92 |
| Experiment-3 | | | | | | | | | | |
| Ratio to the Allain method | 1.00 | 0.98 | 0.98 | 0.97 | 0.98 | 0.97 | 0.95 | 0.93 | 0.87 | 0.86 |

Note:
OPhPEE: octyl phenoxy polyethoxy ethanol
NPhPEE: nonyl phenoxy polyethoxy ethanol
*: OPhPEE having n (average) of 30 was used.

JPAP=Japanese Patent Application Publication No.

| JPA No. 96378/78 | U.S. Pat. No. 4,275,151 |
| --- | --- |
| | U.S. Pat. No. 4,275,152 |
| JPA No. 85200/86 | U.S. Pat. No. 4,680,259 |
| JPA No. 125796/75 | GB 1,479,994 |
| JPA No. 171864/84 | EP 0 119 861A |
| JPA No. 108753/85 | EP 0 142 849A |
| JPP No. 21677/78 | U.S. Pat. No. 3,992,158 |
| JPA No. 90859/80 | U.S. Pat. No. 4,258,001 |
| JPA No. 164356/80 | U.S. Pat. No. 4,292,272 |
| JPA No. 66359/82 | GB 2 087 074A |
| JPA No. 222769/85 | EP 0 162 302A |
| JPA No. 145965/84 | EP 0 115 873A |
| JPP No. 45599/81 | U.S. Pat. No. 3,983,005 |
| JPP No. 25840/80 | U.S. Pat. No. 3,886,045 |
| JPA No. 54962/84 | EP 0 103 901A |
| JPP No. 18628/83 | U.S. Pat. No. 4,042,335 |
| JPA No. 124398/81 | U.S. Pat. No. 4,350,762 |
| JPA No. 155852/81 | U.S. Pat. No. 4,291,121 |
| JPP No. 5519/82 | U.S. Pat. No. 4,089,747 |
| JPA No. 193352/84 | EP 0 122 641A |
| JPA No. 4960/86 | EP 0 165 588A |
| JPA No. 156079/79 | U.S. Pat. No. 4,169,751 |
| JUMP No. 142454/81 | U.S. Pat. No. 4,387,990 |
| JPAP No. 501144/83 | WO 83/00391 |

What is claimed is:

1. A multilayer analysis element for determination of total cholesterol comprising a light-transmissive water-impermeable support, at least one hydrophilic polymer layer provided on said support and a spreading layer provided on said hydrophilic polymer layer(s), and containing in one or more of said layers:

(a) at least one enzyme having cholesterol esterase activity,
   (b) cholesterol oxidase,
   (c) peroxidase,
   (d) a colorimetric reagent composition, which in the presence of hydrogen peroxide and said peroxidase, produces a color change;
   (e) at least one bile acid compound selected from the group consisting of bile acids, bile acid derivatives and salts of said acids and derivatives, and
   (f) an alkyl phenoxy polyethoxy ethanol containing a polyoxyethylene chain composed of 30 to 60 oxyethylene units, wherein the alkyl group in said alkyl phenoxy polyethoxy ethanol is a linear or branched alkyl group having 7 to 10 carbon atoms.

2. The multilayer analysis element of claim 1, wherein said bile acid compound is selected from the group consisting of cholic acid, deoxycholic acid, lithocholic acid, kenodeoxycholic acid, taurocholic acid, glycocholic acid, taurodeoxycholic acid, glycodeoxycholic acid and sodium, potassium and lithium salts of these bile acids.

3. The multilayer analysis element of claim 1, wherein said colorimetric reagent composition comprises a chromogen and a coupler which oxidatively couples with the chromogen in the presence of said peroxidase and hydrogen peroxide, to form a quinoneimine dye.

4. The multilayer analysis element of claim 1, wherein said colorimetric reagent composition comprises a leuco dye which is oxidized by hydrogen peroxide in the presence of said peroxidase to form a dye.

5. The multilayer analysis element of claim 1, wherein the element further contains a buffering agent.

6. The multilayer analysis element of claim 1, wherein the colorimetric reagent composition further contains a compound which contains or releases a ferrocyanide ion.

7. The multilayer analysis element of claim 1, wherein the amount of said bile acid compound is about 0.2 g to about 10.0 g per m$^2$ of the element.

8. The multilayer analysis element of claim 1, wherein the amount of said alkyl phenoxy polyethoxy ethanol is about 0.5 g to about 12.0 g per m$^2$ of the element.

9. The multilayer analysis element of claim 1, wherein the amount of said enzyme having cholesterol esterase activity is about 500 to about 50,000 IU per m$^2$ of the element, the amount of said cholesterol oxidase is about 1,000 to about 30,000 IU per m$^2$ of the element, and the amount of said peroxidase is about 1,000 to about 100,000 IU per m$^2$ of the element.

10. The multilayer analysis element of claim 6, wherein the amount of said ferrocyanide ion is about 0.1 to about 10 millimoles per m$^2$ of the element.

11. The multilayer analysis element of claim 1, wherein a layer of said at least one hydrophilic polymer layer is a water-absorptive layer provided on the support and another layer of said at least one hydrophilic polymer layer is a layer containing the colorimetric reagent composition provided on said water-absorptive layer, and the spreading layer is provided on the layer containing the colorimetric reagent composition.

12. The multilayer analysis element of claim 1, wherein said enzyme having cholesterol esterase activity is contained in the spreading layer.

13. The multilayer analysis element of claim 1, wherein the bile acid compound is contained in a layer the same as or adjacent to a layer containing the alkyl phenoxy polyethoxy ethanol.

14. The multilayer analysis element as claimed in claim 3, wherein the amount of chromogen employed in said colorimetric reagent composition is about 0.5 to about 10 millimoles and the amount of coupler employed in said colorimetric reagent composition is about 2.5 to about 50 millimoles.

15. The multilayer analysis element as claimed in claim 4, wherein the amount of leuco dye employed in said colorimetric reagent composition is about 0.5 to about 10 millimoles.

16. The multilayer analysis element as claimed in claim 1, wherein said at least one hydrophilic polymer layer is a water-absorptive layer and said colorimetric reagent composition is contained in the spreading layer.

17. The multilayer analysis element of claim 1, wherein the at least one bile acid compound is in the same layer as the alkyl phenoxy polyethoxy ethanol and the at least one enzyme having cholesterol esterase activity.

18. The multilayer analysis element of claim 1, wherein the colorimetric reagent composition, the at least one enzyme having cholesterol esterase activity, the peroxidase, the bile acid compound and the alkyl phenoxy polyethoxy ethanol are in the spreading layer.

19. The multilayer analysis element of claim 1, wherein the alkyl group in said alkyl phenoxy polyethoxy ethanol has 8 or 9 carbon atoms.

20. The multilayer analysis element of claim 1, wherein the alkyl group in said alkyl phenoxy polyethoxy ethanol is selected from the group consisting of an octyl group, a 1,2,3,3-tetramethylbutyl group, and a nonyl group.

21. The multilayer analysis element of claim 20, wherein the number of the oxyethylene units in said alkyl phenoxy polyethoxy ethanol is 30 to 40.

22. The multilayer analysis element of claim 1, wherein the amount of said bile acid compound is about 0.2 g to about 10.0 g per m$^2$ of the element, and wherein the amount of said alkyl phenoxy polyethoxy ethanol is about 0.5 g to about 12.0 g per m² of the element.

23. The multilayer analysis element of claim 1, wherein said bile acid compound is selected from the group consisting of cholic acid, deoxycholic acid, lithocholic acid, kenodeoxycholic acid, taurocholic acid, glycocholic acid, taurodeoxycholic acid, glycodeoxycholic acid and sodium, potassium and lithium salts of these bile acids, wherein the amount of said bile acid compound is about 0.2 g to about 10.0 g per m² of the element, and wherein the amount of said alkyl phenoxy polyethoxy ethanol is about 0.5 g to about 12.0 g per m² of the element.

24. The multilayer analysis element of claim 1, wherein the amount of said bile acid compound is about 0.2 g to about 10.0 g per m² of the element, wherein the amount of said alkyl phenoxy polyethoxy ethanol is about 0.5 g to about 12.0 g per m² of the element, wherein the amount of said enzyme having cholesterol esterase activity is about 500 to about 50,000 IU per m² of the element, wherein the amount of said cholesterol oxidase is about 1,000 to about 30,000 IU per m² of the element, and wherein the amount of said peroxidase is about 1,000 to about 100,000 IU per m² of the element.

25. The multilayer analysis element of claim 1, wherein said bile acid compound is selected from the group consisting of cholic acid, deoxycholic acid, lithocholic acid, kenodeoxycholic acid, taurocholic acid, glycocholic acid, taurodeoxycholic acid, glycodeoxycholic acid and sodium, potassium and lithium salts of these bile acids, wherein the amount of said bile acid compound is about 0.2 g to about 10.0 g per m² of the element, wherein the amount of said alkyl phenoxy polyethoxy ethanol is about 0.5 g to about 12.0 g per m² of the element, wherein the amount of said enzyme having cholesterol esterase activity is about 500 to about 50,000 IU per m² of the element, wherein the amount of said cholesterol oxidase is about 1,000 to about 30,000 IU per m² of the element, and wherein the amount of said peroxidase is about 1,000 to about 100,000 IU per m² of the element.

26. The multilayer analysis element of claim 1, wherein the number of the oxyethylene units in said alkyl phenoxy polyethoxy ethanol is 30 to 50.

* * * * *